United States Patent [19]

Widlicka et al.

[11] Patent Number: 5,604,784
[45] Date of Patent: Feb. 18, 1997

[54] RADIATION SHIELD COATING

[75] Inventors: William C. Widlicka, Chardon; Renard J. Passerell, Litchfield, both of Ohio

[73] Assignee: Picker International, Inc., Cleveland, Ohio

[21] Appl. No.: 424,050

[22] Filed: Apr. 19, 1995

[51] Int. Cl.⁶ .................................................. H01J 35/16
[52] U.S. Cl. ........................................ 378/203; 250/515.1
[58] Field of Search ............................. 250/515.1, 506.1, 250/507.1, 516.1, 517.1; 378/203, 204, 193, 162, 140

[56] References Cited

U.S. PATENT DOCUMENTS 3,200,085  8/1965  Guglielmo .
3,618,614  11/1971 Flynn .
3,818,234  6/1974  Atkins et al. ........................ 250/515.1
3,950,572  4/1976  Ayusawa et al. .
4,813,062  3/1989  Gilpatrick .......................... 378/210 X
5,334,847  8/1994  Kromberg .

Primary Examiner—David P. Porta
Attorney, Agent, or Firm—Timothy B. Gurin; John J. Fry

[57] ABSTRACT

Granulated bismuth is mixed with a liquid carrier into a suspension. The carrier-bismuth combination is applied to a surface in a thickness sufficient to provide a desired amount of radiation attenuation. The carrier adheres to the surface and maintains the bismuth adjacent said surface.

20 Claims, 2 Drawing Sheets

Fig.1

RADIATION SHIELD COATING

BACKGROUND OF THE INVENTION

The present invention is related to radiation shield coating in diagnostic x-ray applications. It finds particular application in coating the housing of x-ray tubes or the walls of an x-ray examination room to prevent the unwanted propagation of x-radiation therefrom.

X-ray tubes are used in radiographic or fluoroscopic imaging to produce x-rays that are directed towards an object being imaged. These x-ray tubes are usually enclosed in a housing that, among other things, prevent x-rays from propagating in undesirable directions. To this end, the inside of these housings are usually lined with lead sheets that have been cut from larger sheets of lead and formed to fit along the inside surfaces of the housing. Similarly, rooms in which x-ray examinations are conducted are also lined with lead sheets to prevent unwanted propagation of x-radiation outside of the room.

The use of lead sheets for gamma ray shielding is set forth in U.S. Pat. No. 5,334,847 to Kronberg ('847 patent). Many of the reasons set forth in the '847 for using lead sheets for gamma ray shielding are also applicable to x-ray shielding. Specifically, lead is often used as a shield because it is dense, easily worked, relatively inexpensive and is often smaller than a comparable radiation shield made of almost any other material, and therefore it takes up less space.

A drawback with using lead sheets for radiation shielding, however, is the time required to cut each sheet to an appropriate size and apply the cut sheet to the housing or wall. Another drawback arises in accurately cutting the lead sheet so that there are no voids at a seam or Junction of adjoining sheets when they are applied to the housing or wall. Still another drawback with lead sheets lies in applying a fiat sheet of lead to a curved surface as might occur in a housing for an x-ray tube. Yet another drawback, set forth in the '847 patent, is that lead is a toxic metal that is slowly attacked and corroded by air, water and soil acids. In spite of these drawbacks, however, lead sheets have been successfully and safely used to line the housings of x-ray tubes and the walls of x-ray examination rooms.

In an effort to overcome the above drawbacks other metals that provide radiation shielding have been proposed. One such metal is bismuth which appears next to lead on the periodic table. Some of properties of bismuth include: the density of bismuth is 9.75 grams/cubic centimeter (86% the density of lead); 99%+ purity bismuth is relatively inexpensive; bismuth is relatively brittle; bismuth is immune to corrosion under most environments; and bismuth forms salts that hydrolyze in water to become insoluble and therefore it is virtually non-toxic. Because of its density, bismuth is an effective radiation shield. Moreover, because of its availability, low cost and because it is virtual non-toxic, bismuth is a desirable alternative to lead as a radiation shield. However, because bismuth is relatively brittle, it is difficult to form small sheets of bismuth from larger sheets. Thus, its usefulness is limited in application where custom sheet sizing is required. Such applications include x-ray tube housings and the walls of x-ray examination rooms One use of bismuth in a radiation shielding environment is set forth in the '847 patent wherein bismuth is used as an exterior coating for a container used to transporting or storing radioactive material. Specifically, molten bismuth is applied to the exterior of the container which is made from a material, such as depleted uranium. More specifically, the container is placed in a mold made from a high-melting metal to which bismuth does not adhere, such as stainless steel, and molten bismuth is poured into the mold. The container is positioned in the mold so that the molten bismuth poured into the mold covers the entire surface of the container. The molten bismuth "Hans" with the depleted uranium in a manner similar to the way tin or its alloys coat and adhere to copper or brass. As a result of "tinning", the molten bismuth spreads over the surface of the depleted uranium and adheres strongly to the depleted uranium.

A drawback of using molten bismuth is that a mold is needed to apply the molten bismuth to the housings of x-ray tubes or the walls of x-ray examination rooms. Another drawback is that molten bismuth is used whereas it is desirable to work with bismuth at room temperature.

The present invention contemplates an improved radiation shield coating and method for applying the same that overcomes the above problems and others.

SUMMARY OF THE INVENTION

In accordance with one aspect of the present invention, a radiation shield comprised of granulated bismuth disposed on a surface in a thickness sufficient to produce a desired amount of radiation attenuation is provided. The bismuth is maintained against the surface by a carrier disposed on said surface. The carrier adheres to the surface thereby maintaining the bismuth adjacent the surface.

In accordance with a more limited aspect of the invention the carrier is a liquid adhesive or an adhesive layer.

In accordance with another aspect of the invention, a method of manufacturing a radiation shield is provided. In the method, a coating of granulated bismuth is applied to a substrate. The granulated bismuth is suspended in a carrier and the carrier and bismuth are applied to the substrate by spraying, brushing or rolling the carrier and bismuth onto the substrate.

In accordance with a more limited aspect of the method, the granulated bismuth is applied to the substrate by plasma spraying.

In accordance with another more limited aspect of the method, a liquid adhesive or an adhesive layer in the form of a film having adhesive on both sides is applied to the substrate and is used to maintain the granulated bismuth adjacent said substrate.

In accordance with yet another aspect of the invention, an x-ray enclosure is provided. The enclosure includes a source of x-radiation. A plurality of walls substantially surround the radiation source defining boundaries of said enclosure. Granulated bismuth is disposed on said walls for attenuating the propagation of said radiation.

In accordance with a more limited aspect of the invention, the source of x-radiation is an x-ray tube and the enclosure is a housing for supporting the x-ray tube during operation.

In accordance with yet another more limited aspect of the invention, the enclosure is an examination room and the source of x-radiation is one of a radiographic, fluoroscopic or CT imaging system.

An advantage of using granulated bismuth for radiation shielding is that it is easy to apply and provides the ability to radiation shield complex surfaces or corners seems of adjoining surfaces which, heretofore, required accurate cutting and/or forming of lead sheets.

Still another advantage of the present invention is that the coating thickness can be made thicker where more radiation shielding is needed and thinner where less radiation shielding is needed.

Still yet another advantage of the present invention is that it can be granulated to a finer mesh than lead and therefore granulated bismuth provides more uniform radiation attenuation at thinner coating thickness.

Still other advantages of the present invention will become apparent to those of ordinary skill in the art upon reading and understanding the following detailed description of the preferred embodiment.

BRIEF DESCRIPTION OF THE DRAWING

FIG. 1 is a side view of an spray gun applicator applying a granulated bismuth carrier combination to a curved surface.

THE DETAILED DESCRIPTION OF THE PREFERRED EMBODIMENT

Figure 1:
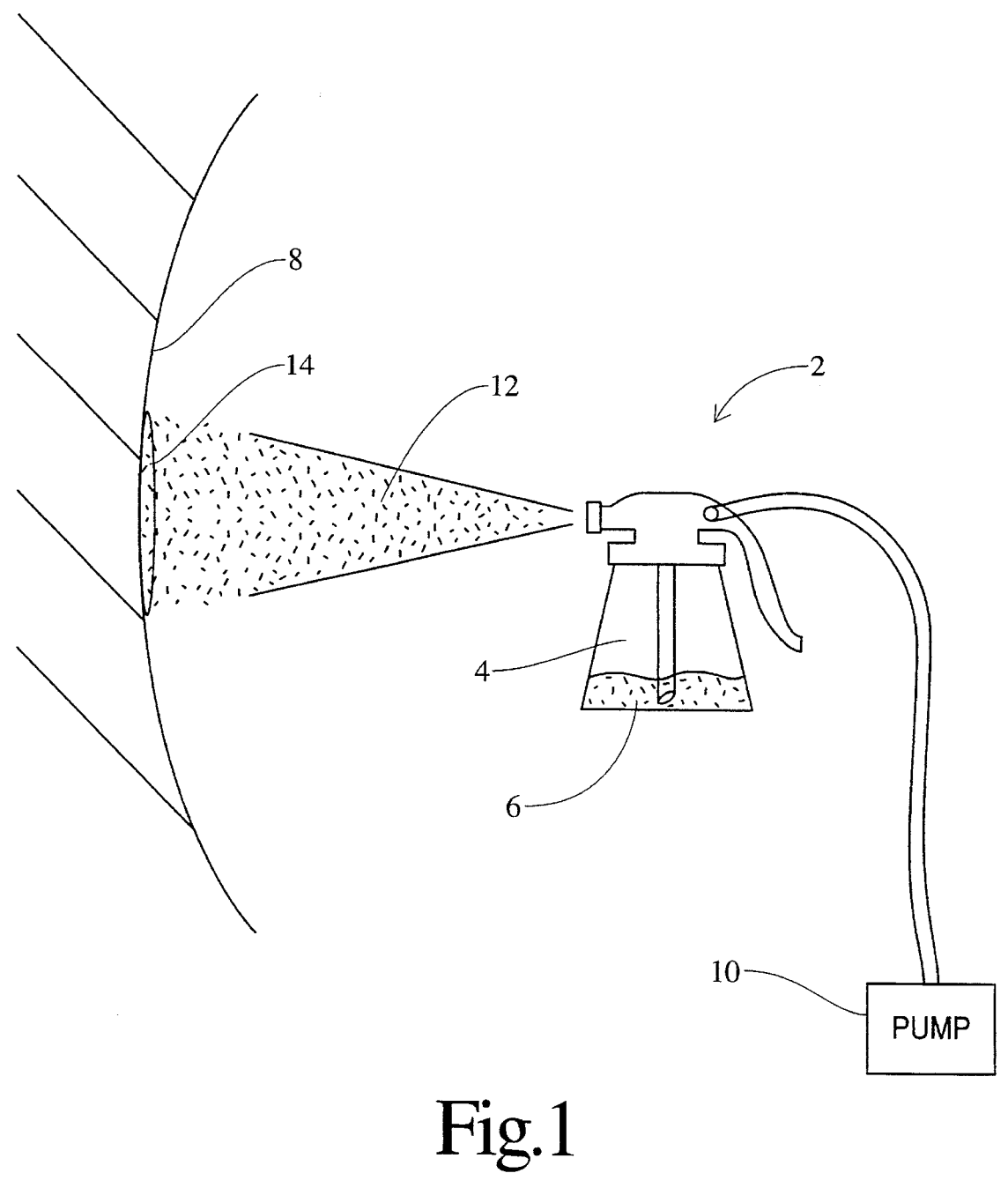
Figure 2:
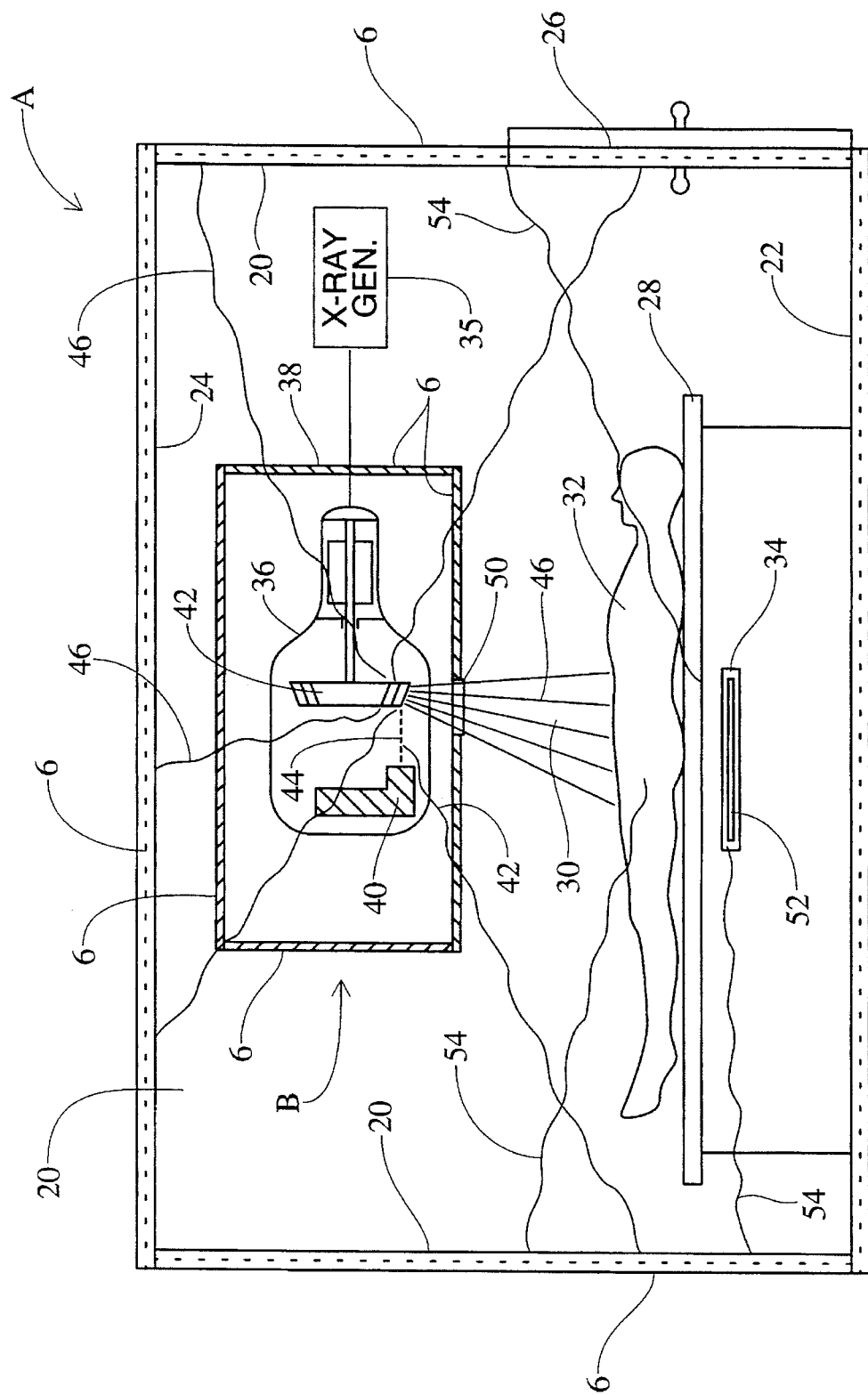
FIG. 2 is a view of an x-ray examination room having a granulated bismuth carrier combination applied to the walls of the room.

Bismuth which has been granulated to a fine mesh by a crusher or other such means is mixed with a liquid carrier into a uniform suspension. The carrier Is selected such that it maintains the bismuth In suspension during application of the bismuth - carrier combination. One such carrier Is a product called Uthane® 55B-E made by AExcel Corporation of Mentor, Ohio. (Uthane® is a registered trademark of AExcel Corporation). With reference to FIG. 1, an applicator 2, such as a spray gun, has a reservoir 4 in which the bismuth - carrier combination 6 Is disposed for application to a surface 8 wherein radiation shielding is desired. To apply the bismuth - carrier combination to the surface, the spray gun Is connected to an air pump 10 or other source of air pressure. The pump forces high velocity air to flow through the spray gun thereby drawing the bismuth - carrier combination from the reservoir and Into the stream of air 12. The output of the spray gun Is directed to the surface 14 such that the bismuth - carrier combination drawn from the reservoir Is deposited thereon.

The carrier, in addition to Its ability to maintain the bismuth in solution, is designed to adhere readily to the surface to which It is applied. In tins manner, the carrier acts as a medium through which the bismuth Is applied to the surface. Specifically, the carrier maintains the distribution of bismuth adjacent to said surface during application and through the curing process. In general, a paint-like carrier is envisioned for the preferred embodiment, however, this is not to be construed as limiting the Invention. Other carriers, liquid or solid, capable of maintaining the granulated bismuth on the surface, are also anticipated.

With reference to FIG. 2, the use of the bismuth - carrier combination In conjunction with a diagnostic x-ray application Is described. In FIG. 2, an x-ray examination room A has a source of radiation B disposed therein. The examination room is defined by walls 20, floor 22 and ceiling 24. An access door 26 is disposed in one of the walls 20 to allow patient and operator access to the room. A patient table 28 is disposed in the room and relative to the radiation source such that a gap 30 is formed therebetween. A patient 32 is disposable on the top of the table and in the gap during examination. An x-ray sensitive screen 34 is disposed in the table to receive radiation from the radiation source impinging thereon.

The radiation source B is comprised of an high voltage generator 35 connected to an x-ray tube 36 for supplying power thereto during the production of radiation. The x-ray tube is disposed in an enclosure 38 that supports the x-ray tube in a position relative to the patient and the patient table. The x-ray tube is conventionally comprised of a cathode element 40 and a rotating anode 42. A beam of electrons 44 generated at the cathode are accelerated towards the anode in a manner well known in the art. The interaction of the electrons and the anode produces x-rays 46 that propagate in a plurality of directions from the face of the anode. To reduce the amount of x-rays propagating in undesirable directions, the inside walls of the x-ray tube enclosure 38 are coated with a sufficient thickness of the bismuth - carrier combination 6 to reduce the amount of x-rays passing through the walls of the x-ray tube to a desirable level. To selectively allow x-rays to leave the enclosure, an x-ray transparent window 50 is disposed in a wall of the enclosure adjacent the anode. In use, the window is oriented towards the gap such that x-rays passing therethrough are directed into the gap.

During the production of radiation during an examination, x-rays pass through the window, through the gap, through the patient, through the table and strike the x-ray sensitive screen. The screen converts the x-rays into visible light in a manner well known in the art. A sheet of photographic film 52, which is more sensitive to visible light than x-rays, is disposed closely adjacent to the screen for recording the visible light image produced by the interaction of the screen with the x-rays for subsequent viewing in a manner well known in the art.

Any radiation passing through the walls of the x-ray tube propagate into the room. Similarly, radiation from the x-ray tube that interacts with materials in its path, such as the patient, produces scattered radiation 54 that propagates in a plurality of directions within the room. To contain the scattered radiation and any radiation that passes through the walls of the x-ray tube, a coating of the bismuth - carrier combination 6 is applied to one or more of the walls, floor and ceiling of the room as required to obtain a desirable level of radiation attenuation. Moreover, a coating of the bismuth - carrier combination is also applied to the door 26 to attenuate radiation impinging thereon. In this manner, radiation produced during an examination is contained within the room to an acceptable level so as to minimize the potential for undesired radiation exposure outside the room. It is to be appreciated that the above describe embodiment is for illustration purposes and is not to be construed as limiting the invention in any manner.

In the preferred embodiment, the bismuth - carrier combination is uniformly applied to a surface requiring radiation shielding. Alternatively, the coating thickness may be varied on a particular surface or on combinations of surfaces. Specifically, the coating thickness is made thicker where more radiation shielding is needed and thinner where less radiation shielding is needed. In this manner the coating thickness can be varied as required by the need to provide radiation shielding.

Bismuth is relatively brittle and therefore is readily granulated. Ideally, bismuth is granulated to an extent that, when applied to the housing or wall, it provides radiation shielding on the same order as a like thickness of a sheet of bismuth. Alternatively, however, the bismuth is granulated to a mesh size wherein a thicker coating of granulated bismuth is required to achieve radiation shielding on the same order as a thinner sheet of bismuth. Moreover, bismuth is more brittle than lead and accordingly is able to be granulated to a finer and more consistent mesh than lead. Because of this, granulated bismuth particles can be disposed closely adjacent to each other thereby forming relatively small spaces between adjacent particles. In contrast, lead, which cannot be granulated to as fine a mesh as bismuth, will have larger gaps between closely adjacent particles relative to bismuth that is granulated to a finer mesh. Accordingly, granulated bismuth can be applied to a surface more densely than granulated lead thereby providing more uniform radiation shielding at thinner coating thicknesses. It is to be appreciated, however, that the mesh size of granulated bismuth is not to be construed as limiting the invention.

A high purity bismuth is contemplated for use in the preferred embodiment. Alternatively, however, lower purity bismuth is acceptable providing a desired amount and uniformity of radiation attenuation is achieved. Specifically, a lower purity bismuth may contain impurities that do not attenuate radiation to the same extent as pure bismuth. Accordingly, a thicker coating of lower purity bismuth may be required to achieve the amount and uniformity of radiation attenuation that a thinner coating of higher purity bismuth achieves.

Because the bismuth is suspended in a liquid carrier it can be applied to curved surfaces by spraying the bismuth - carrier combination onto the curved surface. Alternatively, granulated bismuth can be applied to a desired surface by plasma spraying the bismuth onto a desired surface in a manner known in the art. Specifically, in plasma spraying, the granulated bismuth is drawn into a stream of high velocity and heated gas in much the same manner as the air stream 12 in FIG. 1. The heated gas and bismuth combination strike the surface to which the bismuth is to be applied thereby depositing the bismuth on the surface.

While the above embodiments have been described with regard to spray applications it should be appreciated that the application of bismuth in a liquid carrier can also occur by other suitable methods such as a paint brush or roller. Alternatively, applying the carrier and bismuth to the surface separately is also contemplated. Specifically, the carrier, i.e., adhesive, is applied to the surface and the granulated bismuth is applied to the surface by a spray gun, by sprinkling or other like application means. In yet another alternative, the adhesive or carrier coating is applied after the granulated bismuth is disposed on the surface. In still another alternative, a film having adhesive on both sides is applied to the surface. The side of the film in contact with the surface maintains the film against the surface. Granulated bismuth is applied to the exposed surface of the film wherein the adhesive secures the granulated bismuth to the film and consequently adjacent the surface.

The above invention has been described with reference to the preferred embodiments. Obvious modifications and combinations will occur to others upon reading and understanding the preceding description. It is intended that the invention be construed as including all such modifications and alterations insofar as they come within the scope of the appended claims or the equivalents thereof.

Having described the preferred embodiments the invention is now claimed to be:

1. A radiation protection shield comprising:
   a coating of granulated bismuth disposed adjacent substantially all of a surface in a thickness sufficient to produce a desired amount of radiation attenuation.

2. The radiation shield as set forth in claim 1 wherein said coating further comprises a carrier for maintaining the distribution of bismuth adjacent said surface.

3. The radiation shield as set forth in claim 2 wherein said carrier is curable at room temperature.

4. The radiation shield as set forth in claim 1 wherein the coating has a cured and an uncured state, the coating in its uncured state being suitable for at least one of rolling, brushing, or spraying on the surface, the coating being curable at room temperature.

5. The radiation shield set forth in claim 1 further including an adhesive layer disposed on said surface for maintaining the bismuth thereagainst, the adhesive layer being curable at room temperature.

6. The radiation shield set forth in claim 1 further comprising a film having adhesive disposed on both sides thereof for maintaining the bismuth against the surface.

7. A method of manufacturing a radiation protection shield comprising the step of applying a coating of granulated bismuth to a substrate, the coating being applied over substantially all the surface of the substrate.

8. The method of manufacturing a radiation shield as set forth in claim 7 comprising the further steps of:
   suspending the granulated bismuth in a carrier having a cured and an uncured state;
   applying the carrier in its uncured state to said substrate by one of brushing spraying, and rolling; and
   curing the carrier at room temperature;
   whereby the bismuth is disposed adjacent the substrate.

9. The method of manufacturing a radiation shield as set forth in claim 7 further comprising the step of applying a coating of adhesive on the substrate, said adhesive used for maintaining the granulated bismuth adjacent said substrate.

10. The method of manufacturing a radiation shield as set forth in claim 7 wherein the step of applying the granulated bismuth to a substrate includes plasma spraying the granulated bismuth on the substrate.

11. An x-ray enclosure comprising:
    a source of x-radiation;
    an enclosure substantially surrounding said radiation source, said enclosure having a surface defining a boundary of said enclosure; and
    a coating comprising granulated bismuth disposed on said surface for attenuating the propagation of said radiation.

12. The radiation shield set forth in claim 11 further including an adhesive layer disposed on said surface for maintaining the bismuth thereagainst, the adhesive layer being curable at room temperature.

13. The x-ray enclosure as set forth in claim 11 wherein the granulated bismuth is uniformly disposed on said surface.

14. The x-ray enclosure as set forth in claim 11 wherein the source of x-radiation is an x-ray tube and wherein the enclosure is a housing for supporting the x-ray tube during operation.

15. The x-ray enclosure as set forth in claim 11 wherein the enclosure is a room.

16. The x-ray enclosure as set forth in claim 13 wherein the source of x-radiation is one of a radiographic, fluoroscopic or CT imaging system.

17. The x-ray enclosure as set forth in claim 11 further including an adhesive layer disposed on said surface for sustaining the bismuth adjacent said surface.

18. The x-ray enclosure as set forth in claim 11 wherein said coating further comprises a carrier for maintaining the distribution of bismuth adjacent said surface.

19. The x-ray enclosure as set forth in claim 18 wherein the carrier is curable at room temperature.

20. The x-ray enclosure as set forth in claim 11 wherein the coating has a cured and an uncured state, the coating in its uncured state being suitable for at least one of rolling, brushing, or spraying on the surface, the coating being curable at room temperature.

* * * * *